United States Patent [19]

Marx et al.

[11] Patent Number: 5,440,025
[45] Date of Patent: Aug. 8, 1995

[54] PROCESS FOR SEPARATING NUCLEIC ACID POLYMERS

[75] Inventors: Kenneth A. Marx, Francestown, N.H.; Sukant K. Tripathy, Acton, Mass.

[73] Assignee: University of Massachusetts at Lowell, Lowell, Mass.

[21] Appl. No.: 850,654

[22] Filed: Mar. 12, 1992

[51] Int. Cl.⁶ .................. C07H 1/00; C07H 21/02; C07H 21/04
[52] U.S. Cl. .................. 536/25.4; 435/291; 935/19
[58] Field of Search .................. 935/19; 536/27, 25.4; 435/291; 525/256, 260, 285

[56] References Cited

U.S. PATENT DOCUMENTS

| | | | |
|---|---|---|---|
| 4,302,204 | 11/1981 | Wahl et al. | 23/230.3 |
| 4,644,037 | 2/1887 | Druy et al. | 525/390 |
| 4,657,985 | 4/1987 | Druy et al. | 525/390 |
| 4,734,363 | 3/1988 | Dattagupta et al. | 435/91 |
| 4,851,528 | 7/1989 | Stead et al. | 544/189 |
| 4,864,018 | 9/1989 | Stead et al. | 530/351 |
| 4,957,858 | 9/1990 | Chu et al. | 435/6 |

FOREIGN PATENT DOCUMENTS

| | | |
|---|---|---|
| 0286239A1 | 9/1988 | European Pat. Off. |
| 0304845A2 | 1/1989 | European Pat. Off. |
| WO90/06374 | 6/1990 | WIPO |

OTHER PUBLICATIONS

Minehan et al., *Proc. Amer. Chem. Soc., Div. of Polymeric Mat: Sci. and Eng.*, 64, 341-342 (1991).
Minehan et al., *The FASEB Journal*, 5, A811 (1991).
Wnek, *Proc. Amer. Chem. Soc. Div. of Polymeric Mat: Sci. and Eng.* 64, 338 (1991).
Smith, et al., *Biotechnology and Applied Biochemistry*, 12, 661-669 (1990).

*Primary Examiner*—Douglas W. Robinson
*Assistant Examiner*—Gary L. Kunz
*Attorney, Agent, or Firm*—Hamilton, Brook, Smith & Reynolds

[57] ABSTRACT

A method is disclosed for separating a nucleic acid polymer without substantially denaturing the nucleic acid polymer. The method includes contacting a liquid medium, in which the nucleic acid polymer is disposed, with an electrically conductive polymer substrate. The substrate has an electrical charge which, when the substrate is contacted with said liquid medium, causes at least a portion of the nucleic acid polymer in the liquid medium to bind to said substrate without substantially denaturing the nucleic acid polymer. The substrate is then separated from the liquid medium, whereby the bound nucleic acid polymer is removed from the liquid medium, thereby isolating the bound nucleic acid polymer from the liquid medium without substantially denaturing the nucleic acid polymer.

13 Claims, 3 Drawing Sheets

PROCESS FOR SEPARATING NUCLEIC ACID POLYMERS

BACKGROUND OF THE INVENTION

Deoxyribonucleic acid (hereinafter "DNA") and ribonucleic acid (hereinafter "RNA") are linear polymers of nucleic acids. The importance of isolating DNA and RNA has increased as new medical applications incorporating these nucleic acid polymers are developed. For example, isolated DNA can be used in therapeutic applications, such as for in vivo re-mediation of viral diseases and for conducting assays.

One method employed to separate DNA or RNA from a medium includes contacting the medium with a substrate which selectively binds with the DNA. A substrate, such as a nitrocellulose membrane, can be contacted with a suitable medium in which DNA, for example, is suspended. The nitrocellulose binds with the DNA, after which the substrate is removed from the medium, thereby separating the DNA from the medium. However, DNA and RNA separated by this technique are typically denatured during binding with the substrate. The utility of separating nucleic acid polymers by this method is thereby limited.

Thus, a need exists for separation of nucleic acid polymers, such as DNA and RNA, from a medium by a method and a system which overcome or minimize the above-mentioned problems.

SUMMARY OF THE INVENTION

The present invention relates to a method and system for isolating nucleic acid polymers from a liquid medium without substantially denaturing the nucleic acid polymers.

The method includes contacting a liquid medium, in which a nucleic acid polymer is disposed, with an electrically-conducting polymer substrate, the substrate having an electrical charge which, when the liquid medium is contacted with the substrate, causes at least a portion of the nucleic acid polymer in the liquid medium to bind to said substrate without causing substantial denaturation of the bound nucleic acid polymer. The substrate is separated from the liquid medium, whereby the bound nucleic acid polymer is removed from the liquid medium, thereby separating the bound nucleic acid polymer from the liquid medium without substantially denaturing the nucleic acid polymer.

The system includes an electrically-conducting polymer substrate, having an electrical charge which, when the substrate is contacted with a liquid medium in which nucleic acid polymer is disposed, causes at least a portion of the nucleic acid polymer to bind to said substrate without causing substantial denaturation of the bound nucleic acid polymer. A liquid medium having nucleic acid polymer disposed therein is disposed on the substrate, whereby, upon contacting the medium with the substrate, at least a portion of the nucleic acid polymer binds to the substrate, and whereby, upon removing the substrate from the medium, said bound nucleic acid polymer is separated from the liquid medium by the substrate to which it is bound, thereby separating the nucleic acid polymer from the liquid medium without substantially denaturing the nucleic acid polymer.

This invention has many advantages. For example, a nucleic acid polymer, such as DNA or RNA, is separated from a liquid medium by an electrically-conducting polymer substrate, whereby the nucleic acid polymer can be bound to the substrate without reacting with the substrate. Also, the amount of the nucleic acid polymer separated from the liquid medium can be controlled by the amount of electrical charge at a surface of the substrate. Another advantage of this invention is that the nucleic acid polymer is not substantially denatured during separation from the medium. In addition, the nucleic acid polymer can be separated from the medium without chemical reaction of the nucleic acid polymer.

In other applications, the amount of nucleic acid polymer which binds to the substrate can be varied by changing the amount of oxidatively-formed positive electrical charge on the substrate. The amount of positive electrical charge can be varied, such as by electrochemical oxidation or electrochemical reduction of the polymer at the substrate surface. Nucleic acid polymers can thus be bound to a substrate surface for separation from a medium or for treatment, and then released.

Also, the polymer at the substrate surface can be modified to cause the nucleic acid polymer bound to the surface to react with another reactant or catalyst at the surface to thereby cleave or otherwise modify the nucleic acid polymer. Further, nucleic acid polymers can be purified by binding them to a polymer substrate and separating them from a medium by the method of the invention, rinsing the polymer surface to remove impurities, and then releasing the bound nucleic acid polymers into a second medium, thereby resulting in a purified suspension of the nucleic acid polymers.

DETAILED DESCRIPTION OF THE INVENTION

Figure 1:
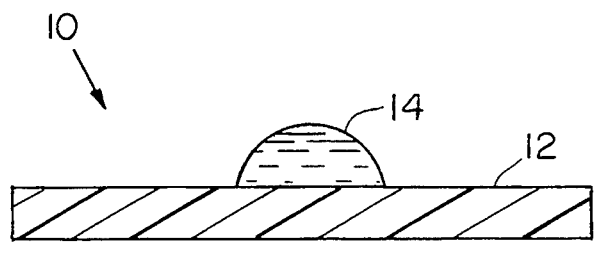
FIG. 1 is a section view of one embodiment of the invention wherein a liquid medium having a nucleic acid polymer disposed therein is disposed on a support.

The features and other details of the method and system of the invention will now be more particularly described with reference to the accompanying drawings and pointed out in the claims. It will be understood that the particular embodiments of the invention are shown by way of illustration and not as limitations of the invention. The principle features of this invention can be employed in various embodiments without departing from the scope of the invention.

The present invention includes a method and system for isolating a nucleic acid polymer, such as DNA or RNA, from a liquid medium by contacting the liquid medium with a suitable electrically-conducting polymer substrate. Examples of suitable electrically-conducting polymers include suitable polyheteroaromatic polymers, polyacetylenes, polyparaphenylenes, polyphenylenevinylenes and suitable derivatives thereof. Preferred substrates include suitably polyheteroaromatic polymers. The term "polyheteroaromatic polymer," as defined herein, means an aromatic polymer having repeating units which include at least two elements in the aromatic rings of the repeating units.

Although the mechanism is not completely understood, it is believed that suitable polymers are electrically conductive because electrochemical oxidation, for example, causes positively charged regions, or "defects," which allow electrons to move along polymer chains which include such defects, thereby conducting an electrical current. Examples of suitable polyheteroaromatic polymers include alkyl-substituted polythiophenes and polypyrrole. A particularly preferred polyheteroaromatic polymer is polypyrrole. The empirical structure of polypyrrole is shown below:

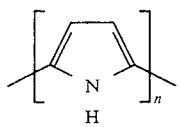

The polymer substrate is formed by a suitable method, such as by electrochemical polymerization. In one example of electrochemical polymerization, a polypyrrole film is formed by disposing a graphite-rod cathode and a platinum-plate anode into a monomer solution of distilled pyrrole. A suitable current density is maintained at a suitable voltage for a sufficient period of time to cause a polypyrrole film to form on the anode.

In a particularly preferred embodiment, the monomer solution includes 0.20M distilled pyrrole, and 0.2M tetraethylammonium p-toluenesulfonate as electrolyte in acetonitrile containing two percent water, by weight. The current density is maintained at about one mA/cm$^2$ and the voltage is maintained at about 1.1 volts for a period of time of about five hours to thereby form a film on the anode. Preferably, the polyheteroaromatic polymer film has a thickness in the range of between about fifty and about one-hundred $\mu$m.

The polymerization reaction of pyrrole to form polypyrrole is shown below:

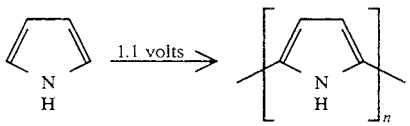

It is believed that the electrically-conducting polymer film, such as a polypyrrole film, has regions of net positive electrical charge which enable binding of a nucleic acid polymer to the surface of the polymer film without substantially denaturing the nucleic acid polymer.

Optionally, the electrically-conducting polymer film can be exposed to conditions which reduce the net average positive electrical charge. In one embodiment, the net positive electrical charge is reduced by exposing a polypyrrole film to conditions similar to those of electrochemical polymerization, but without the presence of monomer in the TE buffer solution. The voltage during reduction of the net positive electrical charge is maintained at about 1.25 volts, for example, for a period of time of about thirty minutes. The net positive electrical charge at the surface of the polypyrrole substrate is thereby reduced. The reduced net positive electrical charge significantly diminishes the amount of nucleic acid polymer which binds to the polypyrrole substrate.

After the polypyrrole film has formed, the electrical current is terminated, and the anode plate and polyheteroaromatic polymer film are removed from the monomer solution. The film is rinsed with a suitable organic solvent and then soaked in the organic solvent for about one hour. Examples of suitable organic solvents include acetonitrile, etc. The polypyrrole film is then separated from the surface of the anode plate and soaked in additional organic solvent for a period of time of about twenty-four hours.

After soaking, the polypyrrole film is cut to form a disk. The disk is then suitably dried to form a substrate. An example of a suitable method for drying the disk is by disposing the disk on weighing paper and then exposing the disk to standing ambient air for a period of time of about one day. In one embodiment, the disk has a diameter of about three millimeters.

In one embodiment of the invention, shown in FIG. 1, system 10 includes support 12. Support 12 is formed of a material which is suitable for supporting a droplet. Examples of suitable materials for forming support 12 include clean glass, plastic, etc. In a particularly preferred embodiment, support 12 is formed of polypropylene.

Droplet 14 includes a medium and a nucleic acid polymer which is to be separated from the medium. An example of a suitable medium is a buffer solution which includes one mM ethylenediamine tetra-acetic acid and ten mM tris(hydroxymethyl) aminomethane (hereinafter "TE buffer solution"), having a pH of about eight.

Suitable nucleic acid polymers include nucleic acid polymers which can be separated from the medium without being substantially denatured. Examples of suitable nucleic acid polymers include single and double stranded DNA and RNA. The nucleic acid polymer can be labeled by a suitable method, such as with radioisotopes, chromogenic enzyme substrates, fluorescent materials, etc.

Figure 2:
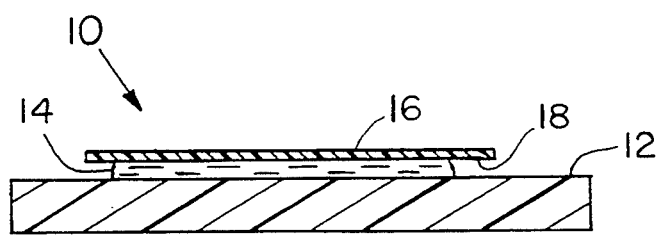
FIG. 2 is a section view of the embodiment shown in FIG. 1, further including a polyheteroaromatic polymer substrate disposed on the medium.

Droplet 14 is disposed on support 12 by a suitable means, such as by manually dispensing droplet 14 from an eyedropper. Polymer substrate 16, shown in FIG. 2, is then disposed onto droplet 14, whereby surface 18 of polyheteroaromatic polymer substrate 16 contacts droplet 14. Suitable polymer substrates include polymer substrates which can bind the nucleic acid polymers without substantially denaturing the nucleic acid polymer. A particularly preferred polymer substrate is formed of polypyrrole.

Contact is maintained between surface 18 and droplet 14 for a period of time sufficient to cause at least a portion of the nucleic acid polymer in droplet 14 to bind to surface 18. A wide variety of contact times are possible (e.g., between about a few hours and a few days). The contact times will depend upon such factors as the concentration of the nucleic acid polymer in the liquid medium, the amount and distribution of positive electrical charge at surface 18 of polymer substrate 16, etc.

It is believed that the net positive electrical charge at surface 18 of polymer substrate 16 is sufficient and suitably distributed to cause an interaction between surface 18 and the nucleic acid polymer in droplet 14, whereby the nucleic acid polymer binds to surface 18 without being substantially denatured by the electrical charge on surface 18 of polymer substrate 16. Possible forms of interaction between surface 18 and the nucleic acid polymer include, for example, groove binding and phosphate electrostatic interaction, etc.

Polymer substrate 16 is then separated from droplet 14, whereby the nucleic acid polymer, which is bound to surface 18 of polymer substrate 16, is removed from droplet 14. Surface 18 can then be washed with a suitable fluid. An example of a suitable fluid is a solution of tris-(hydroxymethyl)-aminomethane and ethylene-diamine-tetraacetic acid. The bound nucleic acid polymer is thereby separated from the medium of droplet 14.

The invention will now be further and more specifically described by the following examples. All parts and percentages are by weight unless otherwise specified.

EXAMPLE I

Polypyrrole was synthesized by electrochemical polymerization in a two-compartment cell. The two-compartment cell consisted of a cathode cell and an anode cell. A graphite-rod cathode was disposed in the cathode cell and a smooth platinum plate, having a flat surface area of about 32.5 cm$^2$, was disposed in the anode cell An standard calomel electrode (hereinafter "SCE") reference electrode was also disposed in the anode cell. The cathode, anode and SCE were connected to a Model 231P potentiostat-galvanostat.

A monomer solution was disposed within the two-compartment cell. The monomer solution included: 0.2M distilled pyrrole, commercially available from the Aldrich Chemical Co., Inc.; 0.2M tetraethylammonium p-toluene sulfonate, commercially available from the Aldrich Chemical Co., Inc.; two percent water; and Optima grade acetonitrile, commercially available from Fisher Scientific, Inc., as a solvent, which contained two percent water, by weight. An electrical current was passed through the monomer solution to polymerize the pyrrole monomer. The electrical current density was one mAmp/cm$^2$ and the voltage was maintained at 1.1 volts versus the SCE. The electrical current was maintained for five hours. A polypyrrole film, having a thickness of about seventy five microns, was formed on the flat surface of the anode during the five hour period.

The electrical current was then disconnected and the metal plate was removed from the pyrrole solution. The polypyrrole film was rinsed and then soaked for one hour in acetonitrile. The polypyrrole film was removed from the acetonitrile and then separated from the metal plate with a razor blade. The polypyrrole film was then soaked in pure acetonitrile for twenty-four hours.

A circular disk was formed from the polypyrrole film by cutting the film with a cork bore. The surface area of one side of the disk was 0.28 cm$^2$. The polypyrrole disk was allowed to dry in standing ambient air by disposing it on weighing paper and storing it in a polystyrene Petri dish in the dark for a period of one day.

A one $\mu$g sample of Hha I digested 0X174 DNA was $^{32}$p end-labeled using a 3' end-labeling kit, commercially available from DuPont New England Nuclear, Inc. The DNA was labeled at the 3-hydroxyl end at 37° C. with alpha $^{32}$P labeled cordecypin 5-triphosphate, catalyzed by terminal deoxynucleotidyl transferase.

After the DNA was radio-labeled, it was disposed in an ethanol bath which caused a DNA precipitate to form. The DNA precipitate was formed in a dry ice-ethanol bath. The DNA precipitate was centrifuged at 12,000 g for fifteen minutes to separate the DNA precipitate from the ethanol. The centrifuged DNA was dissolved in a TE buffer solution which included 1 mM ethylenediamine-tetraacetic acid (EDTA) and 10 mM tris(hydroxy-methyl)aminomethane. The buffer solution was adjusted to a pH of about 8 with hydrochloric acid.

Twenty, forty and eighty nanograms of $^{32}$P end-labeled DNA were each dissolved in 200 microliters of TE buffered solution to form three DNA solutions having concentrations of 0.1, 0.2 and 0.4 nanograms per microliter of DNA, respectively. Twelve droplets of each of the resulting DNA solutions were separately placed on clean polypropylene surfaces. The polypyrrole, described above, were placed on the droplets. The polypyrrole disks were maintained in contact with the droplets at a temperature of about 23° C. to allow DNA in the droplets to bind to the polypyrrole disks. The polypyrrole disks were removed in groups of three from droplets of each DNA solution after various intervals of time. After removing the polypyrrole disks, the disks were washed in a TE buffer solution for twenty minutes. The amount of DNA bound to the polypyrrole disks was measured by measuring the $\beta$-rays from the radio-labeled DNA molecules using a liquid-scintillation counter.

Figure 3:
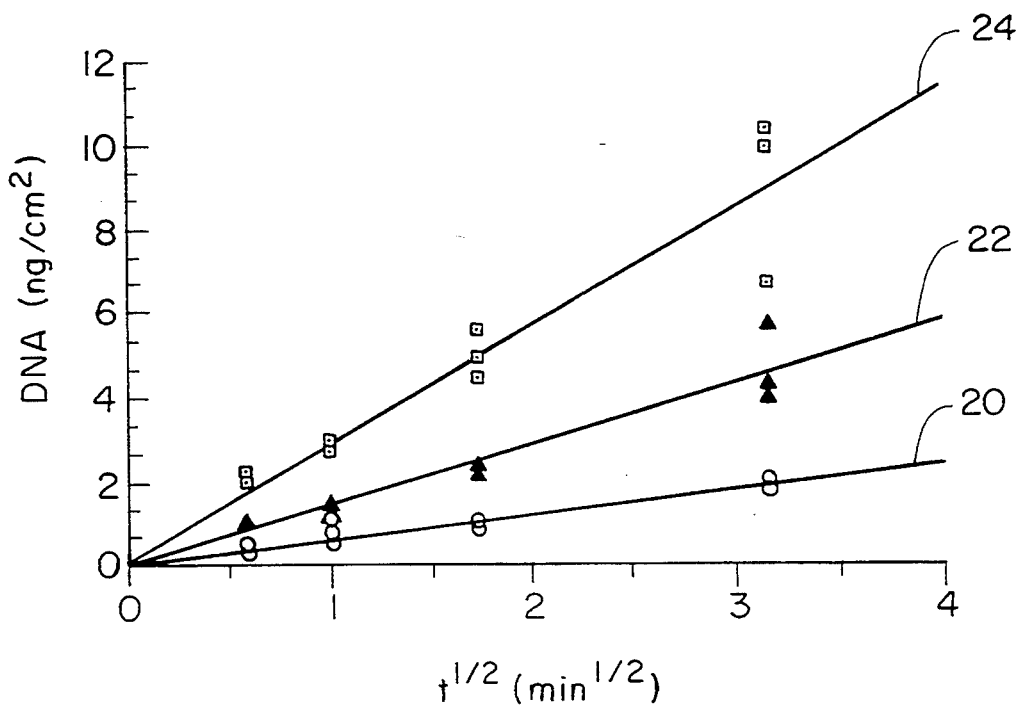
FIG. 3 is a plot of the amounts of DNA separated over a period of time from media having various concentrations of DNA therein by the method and system of the present invention.

FIG. 3 shows the amount of DNA bound to the polypyrrole disks for each of the DNA solutions as a function of time. Lines 20, 22 and 24 represent the amount of DNA isolated from the DNA solution having concentrations of 0.1, 0.2 and 0.4 $\mu$g/ml, respectively.

As shown in FIG. 3, the rate of absorption of DNA onto the polypyrrole was a linear function of the square root of time in minutes. Also, the amount of DNA isolated was directly related to the relative concentration of the DNA in the solution contacting the polypyrrole disks. Both facts together indicate a diffusion-limited binding process which results, without any energetically-dependent conformation change in the DNA. This was corroborated by the low, 5 kcal/mole activation energy measured for this process. In addition, the bound material had a diffusion coefficient of about $10^{-6}$, which is consistent with the expected diffusion coefficient for short fragments of DNA.

EXAMPLE II

A polypyrrole film was formed by the same procedure described in Example I. One-half of the resulting polypyrrole film was then immersed in a solution including 0.2M tetraethylammonium p-toluenesulfonate, two percent distilled water and the remainder acetonitrile. The immersed polypyrrole film was then exposed to chemically-reducing conditions, in which a voltage of 1.25 volts was maintained across the film for thirty minutes to cause the current conducted across the film to diminish from 3.5 to 1.0 mA. Fifteen polypyrrole disks were formed from each half of the polypyrrole film, so that fifteen disks were formed from polypyrrole which had been exposed to chemically-reducing conditions and fifteen disks were formed from polypyrrole which had not been so exposed. Forty nanograms of $^{32}$P labelled DNA was combined with 180 microliters of TE buffer solution to form a DNA solution. Thirty drops of the DNA solution were separately placed on a clean polypropylene surface.

Each of the thirty polypyrrole disks were placed on a droplet to allow DNA in the droplets to bind to the disks. Three unreduced polypyrrole disks and three reduced polypyrrole disks were removed from the droplets over five intervals of time. The removed disks were washed with TE buffer solution and the amount of DNA bound to each of the disks was determined by the method described in Example I.

Figure 4:
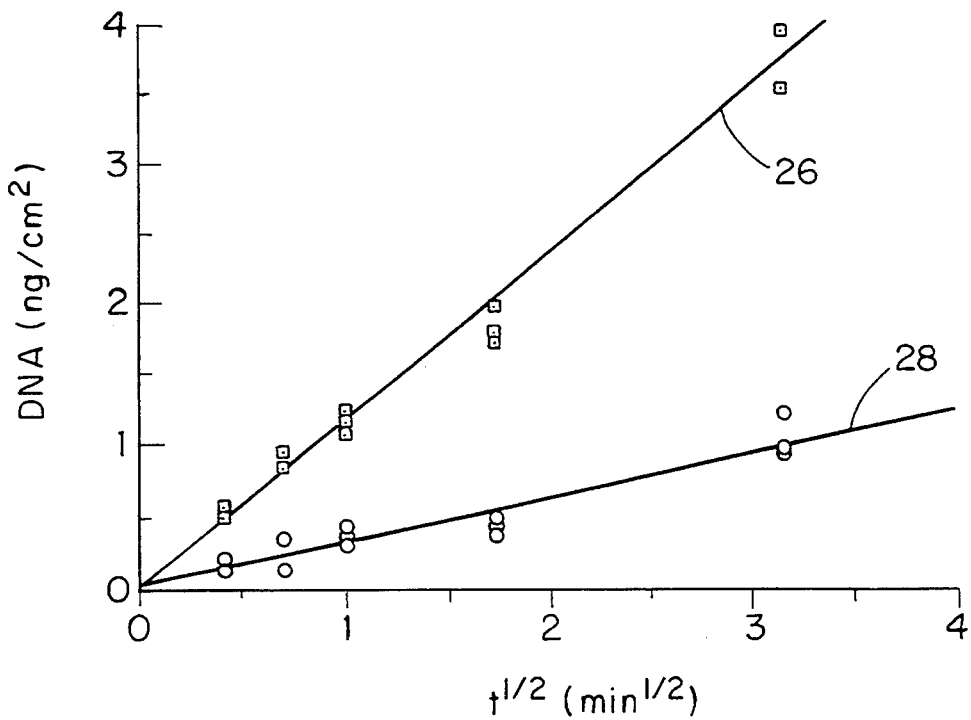
FIG. 4 is a plot of the amounts of DNA separated from a medium over a period of time by the method and system of the present invention, comparing a fully oxidized polypyrrole substrate to a fully oxidized polypyrrole substrate which subsequently has been chemically reduced.

The amount of DNA bound to the polypyrrole disks as a function of time is shown in FIG. 4. Line 26 and line 28 represent the amount of DNA bound to the unreduced and the reduced polypyrrole disks, respectively. As can be seen in FIG. 4, the amount of DNA bound to the unreduced disks was greater than that bound to the reduced disks over the same period of time.

EXAMPLE III

Fifteen polypyrrole disks were prepared by the same method described in Example I. The disks were aged over various periods of time and then contacted with droplets of a DNA solution prepared by the method described in Example II. The period of time of contact between the disks and the droplets was about ten minutes.

Figure 5:
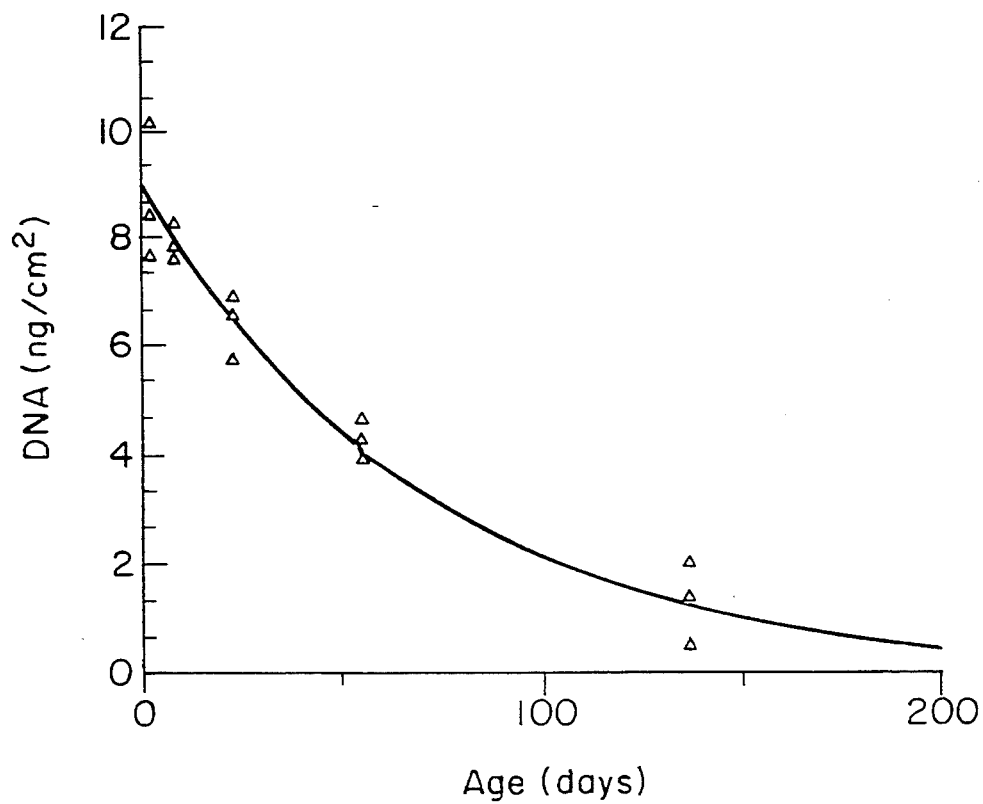
FIG. 5 is a plot of DNA separated from a medium by the method and system of the present invention, wherein the DNA was bound to polypyrrole substrates which had been aged for various periods of time.

The amount of DNA bound to the polypyrrole disks, as a function of the age of the disks, is plotted in FIG. 5. As can be seen in FIG. 5, the amount of DNA which was isolated by binding to the polypyrrole disks was inversely related to the age of the disks. Further, the inverse relationship is exponential.

EXAMPLE IV

The polyalklthiophene, 3-hexadecyl polythiophene and 3-undecylpolythiophene were synthesized in a three neck flask with a dropping funnel. Synthetic grade $FeCl_3$, 0.06 mole was placed in the flask under dry $N_2$. The vessel was evacuated with vigorous agitation of the $FeCl_3$ at 100° C. Dry $N_2$ was introduced to the reaction vessel and 100 ml chloroform was then added under dry $N_2$ flow. 3-Hexylthiophene or 3-undecylthiophene monomer, purchased from TCI America, Inc. (0.02 mole in each case) was added dropwise to the $FeCl_3$ under vigorous agitation using a magnetic stirrer. The reaction mixture was stirred for two days at room temperature. The solution turned blue immediately after addition of the thiophene monomer and took on a deeper color with time (oxidized form). The completed reaction mixture was precipitated into 500 ml methanol. The precipitate was collected by filtration. The precipitate turned dark red after being washed alternately with a large amount of methanol and water and was cleansed successively with methanol in a soxhlet extractor for 20 hours. It was further purified through reprecipitation into methanol (poor solvent) from a sufficient volume of 2-methylhydrofuran. Disks of the polyalkylthiophene polymers were prepared by spin coating from chloroform solution to form 50 $\mu m$ thick films. Substrates of 0.04 $cm^2$ were cut from polymer films using a cork borer and stored until use in DNA binding experiments.

Polypyrrole was electrochemically synthesized and disks cut as in Example I. Experiments to radiolabel DNA and bind the DNA to the substrate disks were carried out exactly as described in Example I except that the DNA was radiolabelled using a different enzyme kit from DuPont New England Nuclear, the Random Primer enzyme kit.

Figure 6:
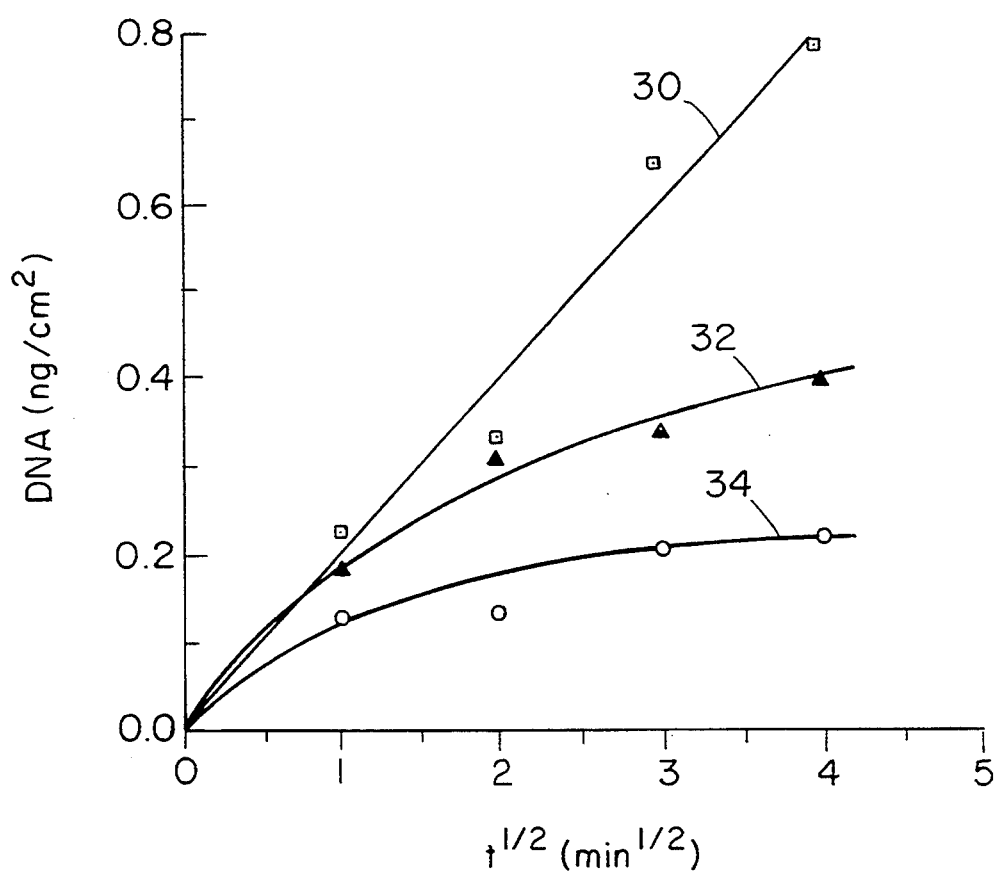
FIG. 6 is a plot of the amount of DNA which was bound to various substrate over time by the method of the present invention.

The results in FIG. 6 show that both polyalkylpyrrole (PPY) (Curve 30) and the two polyalkylthiophenes (PHT and PUT) (Curves 32 and 34, respectively) bind DNA at the 0.2 $\mu g/ml$ 23° C. condition although the time dependence varies slightly for each. The conductivities of the polymer films were found to vary by the four point probe method in the order of their DNA binding ability: PPY at 1.9 S/cm > PHT at 0.020 S/cm > PUT at 0.016 S/cm. This again strongly suggests that the DNA is bound by virtue of the surface functional groups which also give rise to electrical conductivity of the respective polymers.

Equivalents

Those skilled in the art will recognize, or be able to ascertain using no more than routine experimentation, many equivalents to the specific embodiments of the invention described specifically herein. Such equivalents are intended to be encompassed in the scope of the claims.

We claim:

1. A method of separating a nucleic acid polymer from a liquid medium without substantially denaturing the nucleic acid polymer, comprising the steps of:
   a) forming an electrically-conductive polymer substrate by electrochemical deposition, the substrate having sufficient electrooxidation charges to cause at least a portion of a nucleic acid polymer in a liquid medium contacted with the substrate to bind to said substrate without causing substantial denaturation of the bound nucleic acid polymer;
   b) contacting the liquid medium with the electrically-conducting polymer substrate, whereby at least a portion of the nucleic acid polymer in the liquid medium binds to the substrate;
   c) separating said substrate from the liquid medium, whereby the bound nucleic acid polymer is removed from the liquid medium, thereby separating the bound nucleic acid polymer from the liquid medium without substantially denaturing the nucleic acid polymer; and
   d) conducting an electrical current across the substrate having the nucleic acid bound thereto, whereby a sufficient electroreduction potential is placed across the substrate to cause at least a substantial portion of the nucleic acid to be released from the substrate.

2. The method of claim 1 further including the step of applying an electroreduction potential across the substrate prior to contacting the liquid medium with the substrate to thereby diminish the electrooxidation charge on the substrate and the consequent amount of the nucleic acid polymer which will bind to the substrate.

3. A method of separating a nucleic acid polymer from a liquid medium without substantially denaturing the nucleic acid polymer, comprising the steps of:
   a) forming an electrically-conductive polymer substrate by electrochemical deposition, the substrate having sufficient electrooxidation charges to cause, in a subsequent step, at least a portion of a nucleic acid polymer in a liquid medium contacted with the substrate to bind to said substrate without causing substantial denaturation of the bound nucleic acid polymer;
   b) conducting an electrical current across the substrate, whereby a sufficient electroreduction potential is placed across the substrate to reduce the amount of nucleic acid polymer which will bind to said substrate;

c) contacting the liquid medium with the electrically-conducting polymer substrate, whereby at least a portion of the nucleic acid polymer in the liquid medium binds to the substrate; and d) separating said substrate from the liquid medium, whereby the bound nucleic acid polymer is removed from the liquid medium, thereby separating the bound nucleic acid polymer from the liquid medium without substantially denaturing the nucleic acid polymer.

4. The method of claim 3 further including the step of applying an electrical current across the substrate having the nucleic acid bound thereto, whereby a sufficient electroreduction potential is placed across the substrate to cause at least a substantial portion of the nucleic acid to be released from the substrate.

5. The method of claim 1 wherein the electrically-conductive polymer substrate formed includes a polyheteroaromatic polymer component.

6. The method of claim 5 wherein the polyheteroaromatic polymer component is a polypyrrole.

7. The method of claim 5 wherein the polyheteroaromatic polymer component is a polythiophene.

8. The method of claim 1 wherein the electrically-conductive polymer substrate includes a polyparaphenylene component.

9. The method of claim 1 wherein the electrically-conductive polymer substrate includes a polyphenylenevinylene component.

10. The method of claim 1 wherein the electrically-conductive polymer substrate includes a polyacetylene component.

11. The method of claim 1 wherein the nucleic acid polymer includes deoxyribonucleic acid.

12. The method of claim 1 wherein the nucleic acid polymer includes ribonucleic acid.

13. A method of claim 1 further including the step of placing a sufficient oxidation potential across the substrate to form electrooxidized charges on the substrate, whereby the nucleic acid polymer in said liquid medium binds to said substrate.

* * * * *